(12) United States Patent
Souto (10) Patent No.: US 7,977,516 B2
(45) Date of Patent: Jul. 12, 2011

(54) PROCESS OF OBTAINMENT OF TRANS-RESVERATROL AND/OR EMODIN AND NUTRACEUTICAL COMPOSITIONS CONTAINING THEM

(75) Inventor: André Arigony Souto, Porto Alegre-RS (BR)

(73) Assignee: Uniao Brasileira de Educacao e Assistencia-Sponsor of da PUCS, Porto Alegre (BR)

( * ) Notice: Subject to any disclaimer, the term of this patent is extended or adjusted under 35 U.S.C. 154(b) by 0 days.

(21) Appl. No.: 12/523,463

(22) PCT Filed: Jan. 30, 2008

(86) PCT No.: PCT/BR2008/000028
§ 371 (c)(1),
(2), (4) Date: Jul. 16, 2009

(87) PCT Pub. No.: WO2008/092221
PCT Pub. Date: Aug. 7, 2008

(65) Prior Publication Data
US 2010/0081724 A1    Apr. 1, 2010

(30) Foreign Application Priority Data
Jan. 30, 2007 (BR) .................................... 0700152

(51) Int. Cl.
C07C 29/76 (2006.01)
C07C 45/79 (2006.01)
A61K 31/047 (2006.01)
A61K 31/122 (2006.01)

(52) U.S. Cl. .................... 568/810; 568/324; 568/749

(58) Field of Classification Search .................. None
See application file for complete search history.

(56) References Cited

U.S. PATENT DOCUMENTS

| 2004/0052879 A1 | 3/2004 | Ravagnan |
| 2005/0008664 A1 | 1/2005 | Claxton |
| 2006/0135797 A1 | 6/2006 | Maggi |

FOREIGN PATENT DOCUMENTS

| DE | 2159923 | 6/1973 |
| WO | WO 01/03713 | 1/2001 |
| WO | WO 2006/029893 A2 | 3/2006 |

OTHER PUBLICATIONS

Li et al., Dalian Qinggongye Xueyuan Xuebao (2005), 24(3), p. 189-191 (abstract).*
Zhao et al., Zhongguo Yiyuan Yaoxue Zazhi (2006), 26(1), p. 17-18 (abstract).*
Liu et al., Zhongchengyao (2007), 29(4), p. 516-521 (abstract).*
Database CAPLUS on STN, Acc. No. 1998:575341, Kumar et al., Oncogene (1998), 17(7), p. 913-918 (abstract).*
Database CAPLUS on STN, Acc. No. 2000:411675, Manna et al., Journal of Immunology (2000), 164(12), p. 6509-6519 (abstract).*
International Search Report issued in corresponding International Application No. PCT/BR2008/000028 having a filing date of Jan. 30, 2008.

* cited by examiner

Primary Examiner — Brian J Davis
(74) Attorney, Agent, or Firm — Laurence P. Colton; Smith Risley Tempel Santos LLC (57) ABSTRACT

Processes for the separation and purification of polyphenol trans-resveratrol and/or anthraquinone emodin from *Polygonum cuspidatum* and/or *Rumex acetosa*, by means of solvent selective extraction. Products obtained by this process present high level of purity; being therefore useful in the preparation of nutraceutical (pharmaceutical and/or food) compositions with antioxidant, anti-inflammatory, antiviral, cardioprotective, neuroprotective, chemoprotective activities, besides protecting against infections and ischemia, treating type 1 and 2 diabetes, reducing obesity and preventing aging. Useful phytomedicines for the same therapeutic activity and prepared from the roots and/or rhizomes of *Rumex acetosa* or from their fractions are also provided.

13 Claims, 5 Drawing Sheets

PROCESS OF OBTAINMENT OF TRANS-RESVERATROL AND/OR EMODIN AND NUTRACEUTICAL COMPOSITIONS CONTAINING THEM

STATEMENT OF RELATED APPLICATIONS

This application is the U.S. National Phase under Chapter II of the Patent Cooperation Treaty (PCT) of PCT International Application No. PCT/BR2008/000028 having an International Filing Date of 30 Jan. 2008, which claims priority on Brazilian Patent Application No. PI0700152-5 having a filing date of 30 Jan. 2007.

BACKGROUND OF THE INVENTION

1. Technical Field

The present invention relates to methods of separation and purification of trans-resveratrol and/or emodin from plant extracts with increased level of purity, as well as to nutraceutical and/or phytotherapic compositions containing the same. More precisely, the present invention relates to methods of separation and purification of the polyphenol trans-resveratrol and/or anthraquinone emodin of *Polygonum cuspidatum* and/or *Rumex acetosa* (Chinese plants) by selective extraction of solvents. The present invention also relates to phytomedicines prepared from roots and/or rhizomes of *Rumex acetosa* or from their fractions.

2. Related Art

The anthraquinone emodin (3-methyl-1,6,8-trihydroxyanthraquinone) is known for inhibiting the activity of several protein tyrosine kinases, such as $p56^{lck}$, Her2-Neu and so forth. It is also known for inhibiting tumor cell growth, in various leukemic cell lines (U937, HL-60), and for playing a role in chemotherapy-resistance.

Trans-resveratrol (3,5,4'-tri hydroxystilbene) presents antioxidant, anti-inflammatory, antiviral, cardioprotective, neuroprotective, and chemoprotective activities. Besides protecting against infections and ischemia, it treats type 1 and 2 diabetes, reduces obesity and prevents aging. Resveratrol is a polyphenol found mainly in red grape skin and red wine. The more intense wine or grape color, the bigger the polyphenol content is. Studies seem to indicate that resveratrol can lower levels of low-density lipoproteins, also known as cholesterol LDL or "bad" cholesterol, and increase levels of high-density lipoproteins, cholesterol HDL, or "good" cholesterol. Especially when in an oxidized state, LDL can be retained in blood vessel walls resulting in the formation of atheroma plaques. These plaques cause atherosclerosis, which leads to blood vessel obstruction. Resveratrol stimulates HDL production by the liver, decreases LDL production and avoids circulating LDL oxidation, and therefore plays a role in lowering the risk of cardiovascular disorders, such as myocardial infarct.

The plant *Polygonum cuspidatum* (itadori, huzhang, Mexican-bamboo Japanese knotweed) comes from China and is known for having a good amount of resveratrol. In general, resveratrol may be separated and purified from the extracts of *Polygonum cuspidatum* by chromatography: a) in silica gel; b) in macroporous adsorption resin; c) in cellulose; d) in high-speed countercurrent; and e) in polyamide. These methods use sophisticated equipment and solvent mixtures that make solvent recovery difficult.

Emodin, as well, may be separated and purified from the extracts of *Polygonum cuspidatum* by chromatography: a) in silica gel; and b) in high-speed countercurrent. These methods use sophisticated equipment and solvent mixtures that make solvent recovery difficult.

The extracts of *Polygonum cuspidatum* sold nowadays in Brazil are imported, have a low concentration of trans-resveratrol (~8%) and are contaminated by anthraquinone emodin (~5%), which presents color and an undesirable side effect (laxative). In pharmaceutical formulations or food product compositions, where a concentration of 10-20% of trans-resveratrol is required, the presence of emodin is undesirable and inappropriate. Most methods of separation and purification use chromatographic systems that need expensive equipment and solvent mixture that make solvent recovery difficult. The present invention solves these problems by presenting simple and effective methods of separation and purification of polyphenol trans-resveratrol and/or emodin from different plant sources. Those skilled in the art and the manufacturers of pharmaceutical and/or food formulations use trans-resveratrol as an active and/or functional component in such formulations, referred to in the present invention as nutraceutical (pharmaceutical and/or food) compositions because of their properties and benefits. Some sources of trans-resveratrol are presented in Table 1.

TABLE 1

| Known sources of trans-resveratrol* | |
| --- | --- |
| Source | Trans-resveratrol conc. |
| Grape (*Vitis* spp) | 0.16-3.54 µg g$^{-1}$ |
| Peanut (*Arachis hypogaea*) | 0.02-1.92 µg g$^{-1}$ |
| Pistachio (*Pistacia vera*) | 0.09-1.67 µg g$^{-1}$ |
| Common hop (*Humulus lupulus*) | 0.5-1 µg g$^{-1}$ |
| Blueberry (*Vaccinium corymbosum*) | ~32 ng g$^{-1}$ |
| Rhubarb (*Rheum rhaponticum*) | 3.9 mg g$^{-1}$ |
| Japanese knotweed (*Polygonum cuspidatum*) | 0.524 mg g$^{-1}$ |

*Adapted from Nature Reviews Drug Discovery. 2006, 5: 493-506.

The present inventors, in the search for alternative and more available sources of trans-resveratrol and/or emodin, also developed a method for obtaining such actives from sorrel, whose use was not known for this purpose. Sorrel (*Rumex acetosa*), also called common or garden sorrel and spinach dock, is a perennial plant in the family Polygonaceae, with sagitate leaves, reddish flowers forming a panicle, and capsular fruits. Native of Europe and Asia, and exotic in Brazil, it is not taxonomically classified in Brazil (see http://www.ncbi.nlm.nih.gov/Taxonomy/Browser/wwwtax-.cgi?id=41241, or Global Biodiversity Information Facility, whose data are available at http://www.secretariat.gbif.net/portal/ecat_browser.jsp? termsASCCpted=true). It is cultivated because of its edible leaves, the red dye extracted from its roots, and some medicine uses presented in the present invention. Its leaves taste like vinegar due to the oxalic acid. In folk culture, it has anti-scurvy, laxative, and diuretic uses. In literature, the presence of trans-resveratrol in the roots of *Rumex acetosa* was not reported. Only hydroxyanthraquinones were identified and isolated from its roots (Agric. Biol. Chem. 1982, 46, 1913-1914). The only reports about trans-resveratrol in similar plants were described for Rumex bucephalophorus, a plant from Israel, in which trans-resveratrol was 0.165 mg/g (J. Nat. Prod. 2003, 66, 1270-1272; J. Agric. Food Chem. 2006, 54, 1243-1247).

Patent literature comprises some documents related to methods of separation and/or purification of emodin and/or trans-resveratrol. Although none of the documents anticipates or even indirectly suggests the inventive concept of the present invention, some of them are mentioned hereinbelow.

United States patent publication US 2006/0135797 relates to a method for obtaining diacerein with low aloe-emodin content. Initially, a weak base, preferably an organic one, is added to diacerein; then the aqueous solution of the salt formed is subjected to continuous or discontinuous extraction in a water-immiscible solvent (preferably ethyl and butyl acetate, toluene and xylene); and purified diacerein is precipitated by acidification. Although this method also uses emodin extraction with toluene, it is different from the present invention because it adds a weak base to diacerein before the extraction. On the other hand, in the present invention, the extract of *Polygonum cuspidatum* is just washed and dried to be extracted with toluene. Thus, although both methods have a common factor, they are different as a whole.

United States patent publication US 2004/0052879 describes an extraction method for products with pharmacological activity, especially those having antitumor activity, that come from spermatophyte plants. Such products are complex mixtures of compounds, such as cis-resveratrol and trans-resveratrol. Extraction is carried out in a neutral ambient with aliphatic alcohol, preferably methanol or ethanol. Solvent and material are stirred and the product is extracted in an oxygen-free and nitrogen saturated atmosphere. Final extract is then centrifuged, separated from the solid part, and concentrated under vacuum at low temperatures, with ethyl acetate or similar solvents.

United States patent publication US 2005/0008664 relates to formulations with emodin and/or its derivatives. More specifically, a lipid formulation contains emodin, providing emodin solubility in a pharmaceutical formulation.

Japan patent application JP 2005/281179A relates to a purification method for the extract of *Reynoutria japonica* Houtt using a liquid mixture of hydrophilic polar solvent, such as ethanol in water. Extract undergoes absorption with activated charcoal, and then desorption of activated charcoal by a polar solvent, in order to obtain resveratrol selectively with a high level of purity.

Document WO 01/03713A1 describes an extraction method for resveratrol and/or ε-viniferine in vines. This method comprises primary extraction and purification stages, preferably followed by secondary purification. Purified extract is distinguished by having a high content of resveratrol and/or ε-viniferine.

Among several technical advantages of the present invention are the separation and purification of emodin and/or trans-resveratrol with high levels of purity in a unique method and the preparation of phytomedicines from alternative and more available material.

BRIEF SUMMARY OF THE INVENTION

In one aspect of the invention, being, therefore, one of its objects, an improved method for the separation of trans-resveratrol and emodin from plant sources is provided.

In a preferred aspect of the invention, being, therefore, another of its objects, an improved method for the separation of trans-resveratrol and emodin from *Polygonum cuspidatum* by selective extraction of solvents is provided.

In another aspect of the invention, being, therefore, another of its objects, a resveratrol-rich phytomedicine is provided. This phytomedicine is prepared from roots and/or rhizomes of *Rumex acetosa* or from their fractions.

In another preferred aspect of the invention, being, therefore, another of its objects, an improved method for the separation of trans-resveratrol and emodin from roots of *Rumex acetosa* by solvent selective extraction is provided.

In another aspect of the invention, the active trans-resveratrol and/or emodin are obtained in good amounts with a high level of purity, and are directly incorporated into nutraceutical compositions. Emodin inhibits the activity of several protein tyrosine kinases and the growth of tumor cells, and is used as adjuvant in chemotherapy-resistance. Trans-resveratrol presents antioxidant, anti-inflammatory, antiviral, cardioprotective, neuroprotective, and chemoprotective activities, besides protecting against infections and ischemia, treating type 1 and 2 diabetes, reducing obesity and preventing aging. It is, therefore, another object of the present invention to provide nutraceutical compositions with trans-resveratrol and/or emodin obtained from the method of the invention.

These and other objects of the present invention will be understood and appreciated from the detailed description of the invention and the claims attached.

DETAILED DESCRIPTION OF PREFERRED EMBODIMENTS

One aspect of the present invention fills a gap in the state of the art by providing a unique method for separation and purification of emodin and/or trans-resveratrol by which both products are obtained with high level of purity.

Other aspects of the invention, such as the high purity of such active principles and their isolation from different and/or new plant sources, provide an advantageous use in the formulation of nutraceutical compositions, which, in the present invention are understood as to be pharmaceutical and/or food compositions whose active principles are obtained according to the invention. The products obtained by the method far of the invention are active principles that, when added to nutraceutical compositions provide antioxidant, anti-inflammatory, antiviral, cardioprotective, neuroprotective, and chemoprotective activities, besides protecting against infections and ischemia, treating type 1 and 2 diabetes, reducing obesity and preventing aging The following examples aim to illustrate, but not to limit, the preferred embodiments of the invention.

Example 1

Obtaining Trans-Resveratrol from an Imported Extract of *Polygonum cuspidatum*

The method for obtaining the present preferential compounds consists of solid-liquid extraction, Soxhlet type or similar, from the extract of *Polygonum cuspidatum* with different solvents. The first solvent used is toluene during a period of 2-40 hours for extracting mainly anthraquinone. Solvent is cooled at room temperature for obtaining emodin crystals (3-methyl-1,6,8-trihydroxyanthraquinone) with a yield of 4-6% and purity of 91-96%. The second solvent is hexane or petroleum ether for washing during a period of 1-2 hours in order to eliminate impurities. The third solvent is diethyl ether during a period of 2-24 hours. Solvent is evaporated to obtain trans-resveratrol (3,5,4'-trihydroxiestilbeno), with a yield of 5-7% and purity of 92-98%. For this preferred embodiment, the imported extract of *Polygonum cuspidatum* was acquired from Galena Química e Farmacêutica Ltda. Solvents were acquired from specialized companies, all of them of analytical grade. Solid-liquid extractions were performed in Soxhlet standard apparatus (Vogel's Textbook of Practical Organic Chemistry, $5^{th}$ Edition, 1996). This method was followed by Fourier Transform Infrared—Attenuated Total Reflectance (FTIR-ATR) spectroscopy. Products were identified by High Performance Liquid Chromatography (HPLC) and by FTIR-ATR.

The level of purity of the isolated products was determined by:

a) Spectral Correlation Coefficient (SCC), according to the equation below, of FTIR-ATR spectra of the products isolated from extractions and FTIR-ATR spectra of commercial emodin (Sigma) and trans-resveratrol (Sigma).

$$\text{Correlation} = \frac{\Sigma w_i A_i B_i}{(\Sigma w_i A_i A_i)^{1/2} \times (\Sigma w_i B_i B_i)^{1/2}}$$

where $A_i$ and $B_i$ are the absorbance values in spectra A and B at a frequency, i and $w_i$ are the weight of the filters used. When SCC is equal to 1, the spectra are perfected related, and when SCC is equal to zero, both spectra are not related.

b) HPLC, comparing the known concentrations of the products isolated from extractions with the known concentrations of commercial emodin and trans-resveratrol.

Figure 1:
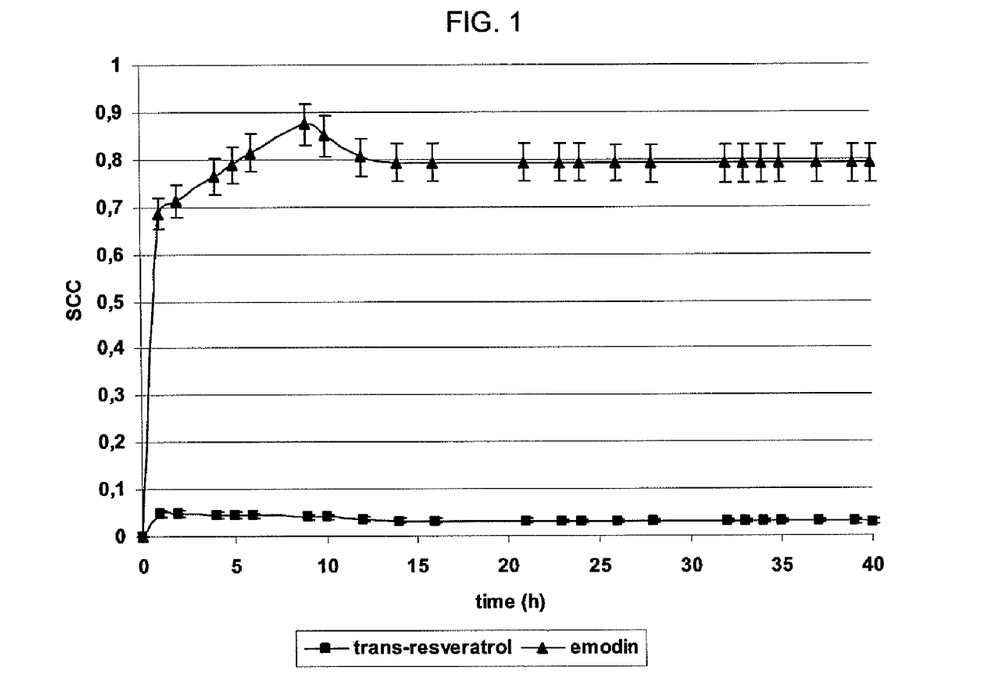
FIG. 1 presents FTIR-ATR monitoring of the solid-liquid extraction of the extract of *Polygonum cuspidatum* in toluene. Spectral Correlation Coefficient (SCC) was determined between the standard spectra of trans-resveratrol and emodin and the spectra of the several extraction times.
Figure 2:
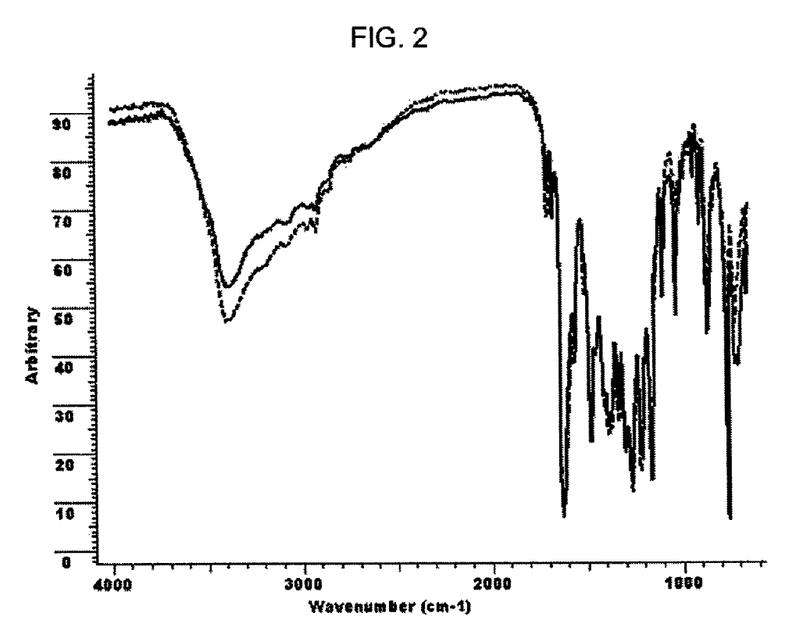
FIG. 2 shows a comparison between the FTIR-ATR spectra of standard emodin (continuous line) and the final product spectrum of the extraction with toluene (discontinuous line). SCC between both spectra is 0.96.
Figure 3:
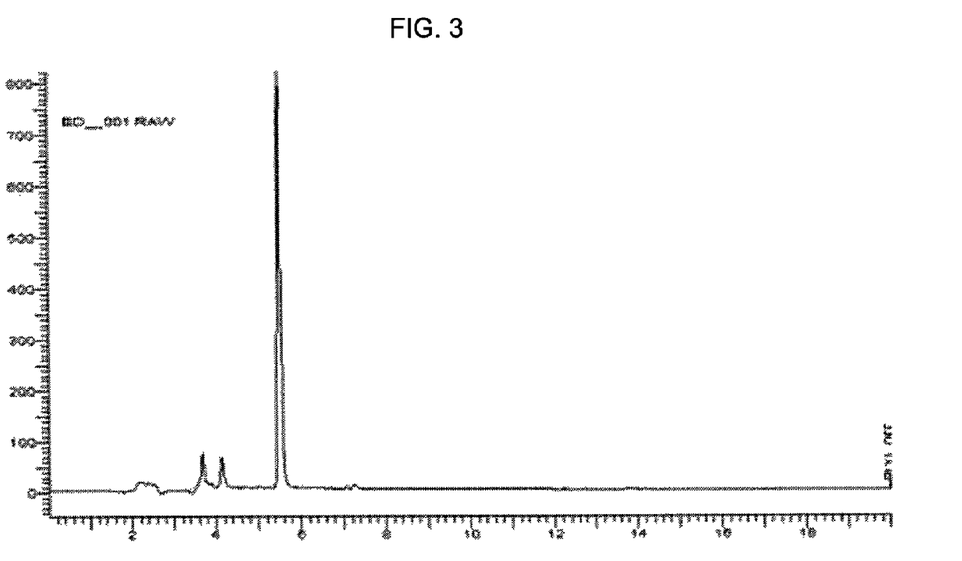
FIG. 3 presents a final product chromatogram of the extraction with toluene in chromatographic column C18 of 250 mm×4.6 mm d.i., particles of 5 μm. The mobile phase, initially composed by water (pH=3)-acetonitrile (65:35, v/v), goes to 100% of acetonitrile, in a linear gradient, for 15 min, with an output of 1.0 mL/min.

For a better description of the separation and purification method of trans-resveratrol and emodin of the present preferential accomplishment, the following phases are described in detail:

*Polygonum cuspidatum* extract (100 g) was weighted and washed with 200 mL of water. Product was dried at room temperature and then put in a paper cartridge, in the Soxhlet apparatus, and extracted with 500 mL of toluene. Every hour, samples were collected to FTIR-ATR analysis, 40 hours in total, as shown in FIG. 1. Extracted product was cooled at room temperature to crystallize 4 to 6 g of emodin (3-methyl-1,6,8-trihydroxyanthraquinone) with a purity of 96% by FTIR-ATR, according to FIG. 2, and of 91% by HPLC, according to FIG. 3.

The product that remained in Soxhlet was extracted with 500 mL of hexane or petroleum ether during a period of 1-2 hours to eliminate impurities.

Figure 4:
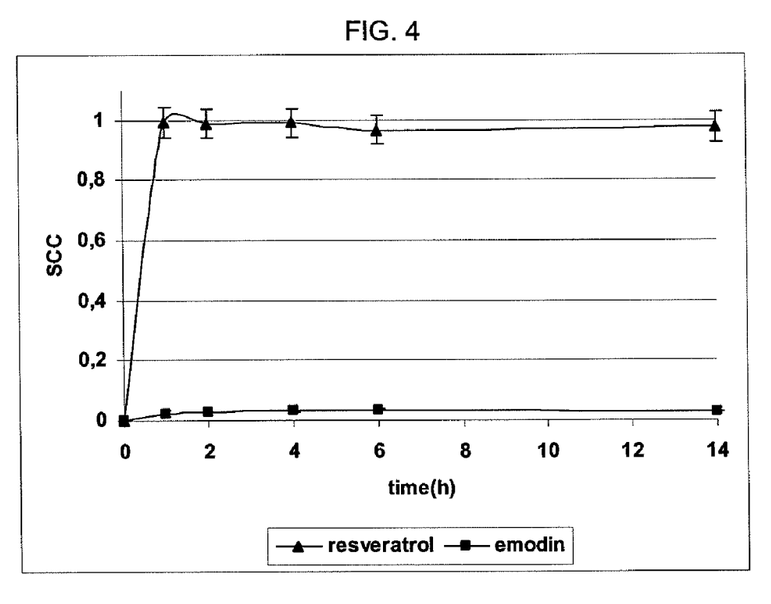
FIG. 4 presents FTIR-ATR monitoring of the solid-liquid extraction of the extract of *Polygonum cuspidatum* in diethyl ether. SCC was determined between the standard spectra of trans-resveratrol and emodin and the spectra of the several extraction times.

The product that remained in Soxhlet was extracted with 500 mL of diethyl ether. Every hour, samples were collected to FTIR-ATR analysis, 14 hours in total, as shown in FIG. 4.

Figure 5:
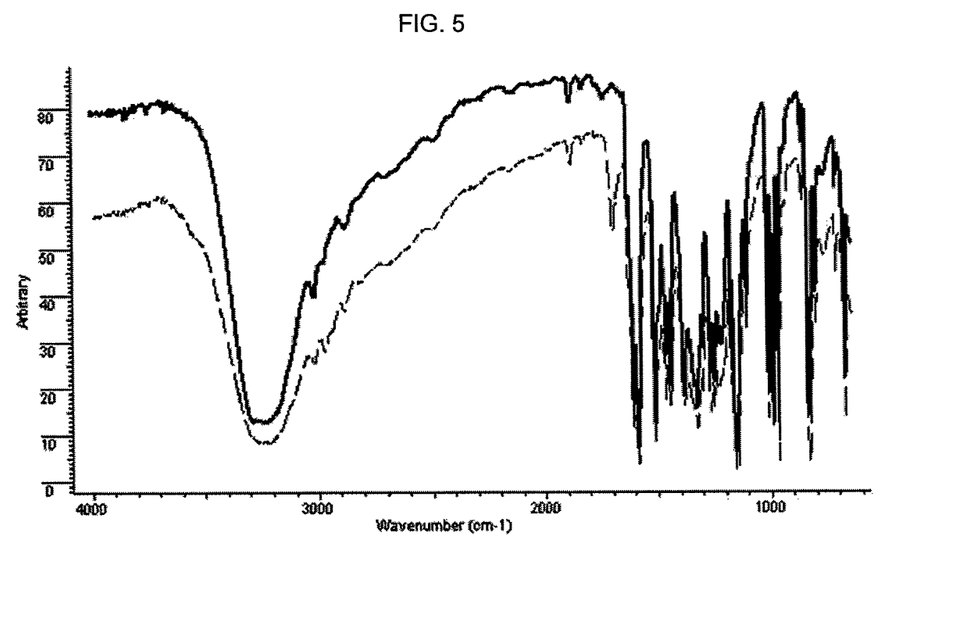
FIG. 5 shows a comparison between the FTIR-ATR spectra of standard trans-resveratrol (continuous line) and the final product spectrum of the extraction with diethyl ether (discontinuous line). SCC between both spectra is 0.98.
Figure 6:
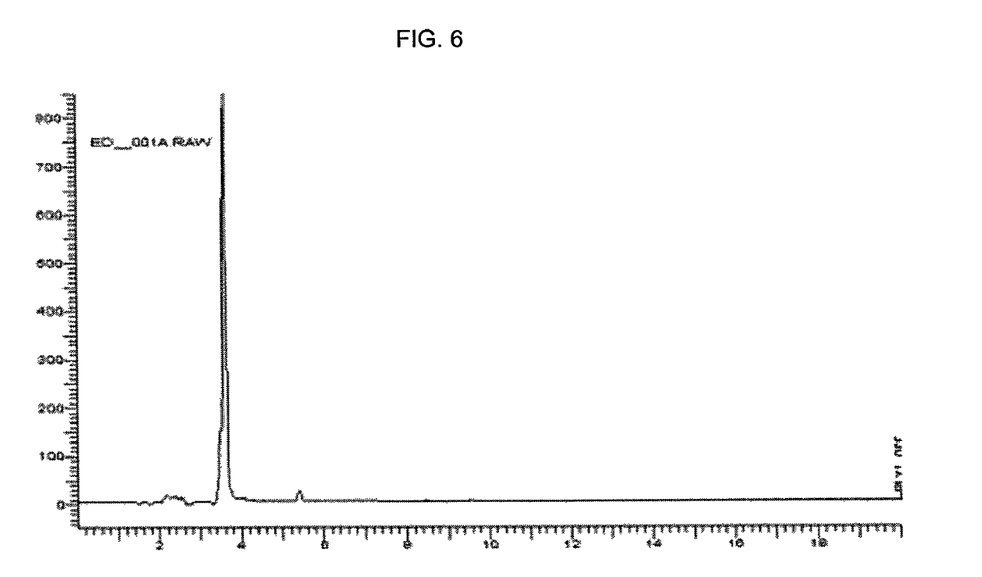
FIG. 6 shows a final product chromatogram of the extraction with diethyl ether in chromatographic column C18 of 250 mm×4.6 mm d.i., particles of 5 μm. The mobile phase, initially composed by water (pH=3)-acetonitrile (65:35, v/v), goes to 100% of acetonitrile, in a linear gradient, for 15 min, with an output of 1.0 mL/min.

From the extracted product solvent was removed under reduced pressure to obtain 5 to 7 g of trans-resveratrol (3,5,4'-trihydroxystilbene) with a purity of 98% by FTIR-ATR (FIG. 5) and of 92% by HPLC (FIG. 6).

Example 2

Obtaining Trans-Resveratrol from Roots of *Rumex acetosa*

Figure 7:
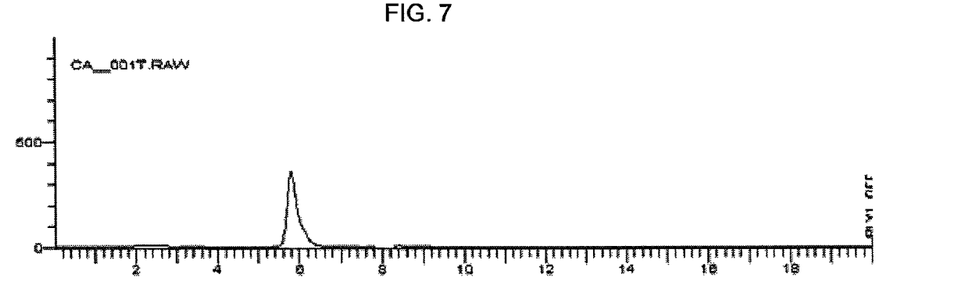
FIG. 7 shows a chromatogram of a standard 100 ppm trans-resveratrol with retention time of 5.90 min.
Figure 8:
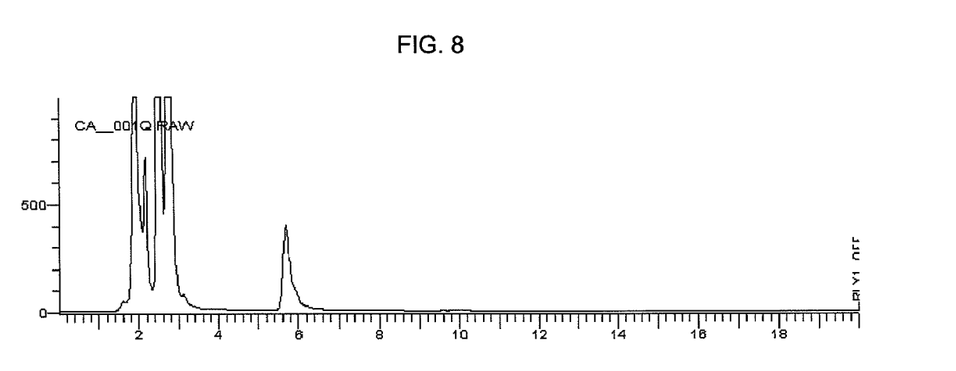
FIG. 8 shows a chromatogram of ethanol extract of the root of *Rumex acetosa* diluted 100 times. Retention time of 5.85 min.
Figure 9:
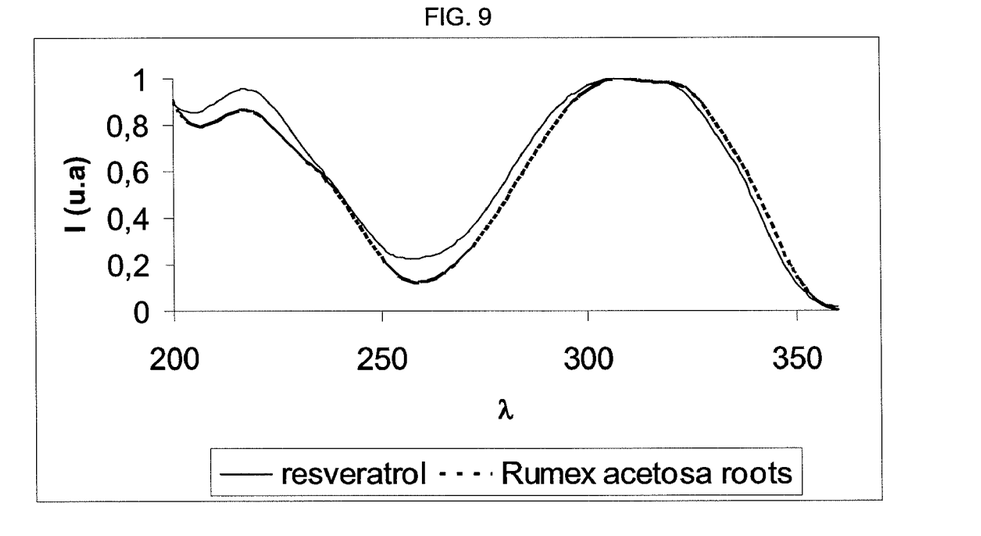
FIG. 9 shows ultraviolet spectra of the chromatogram peaks of standard trans-resveratrol ($t_R$=5.90 min, continuous line) and of the root extract of *Rumex acetosa* ($t_R$=5.85 min, discontinuous line).
Figure 10:
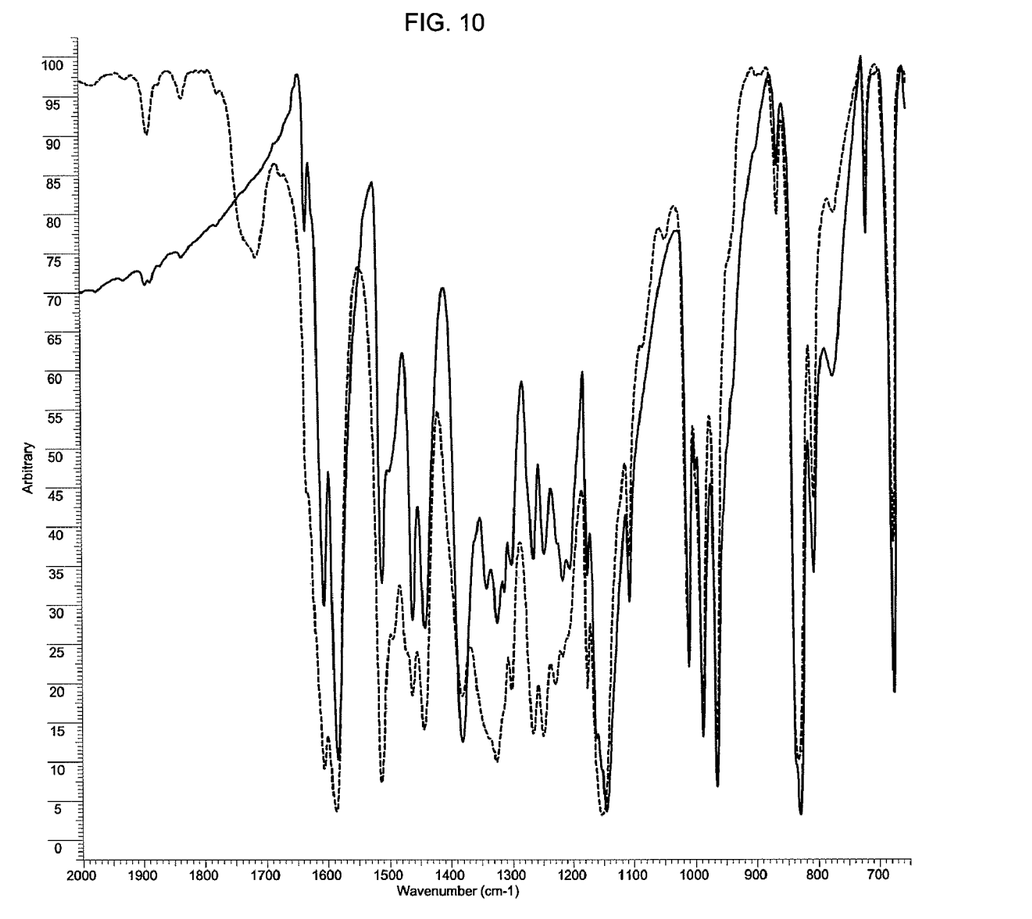
FIG. 10 shows a comparison between the FTIR-ATR spectra of standard trans-resveratrol (continuous line) and the isolated product spectrum of *Rumex acetosa* (discontinuous line). SCC between both spectra is 0.95.

Plant vegetal material was obtained at Pontifical Catholic University of Rio Grande do Sul. *Rumex acetosa* roots (5 g) were washed and extracted with a solution of ethanol/water (70:30) for 15 minutes under stirring. The obtained material was centrifuged at 1000 g for 10 minutes, filtered in a 0.45 µm pore diameter membrane, and then subjected to High-Performance Liquid Chromatography. The analyses were performed in a Perkin Elmer HPLC chromatograph equipped with UV-VIS detector and a $C_{18}$ column, 5 µm 250×4.6 mm. *Rumex acetosa* extract was diluted 100 times with eluent and 20 µL were injected and detected in 306 nm. HPLC chromatography was carried out in isocratic elution (flow of 1.0 mL/min$^{-1}$), with an aqueous solution of 25% acetonitrile, pH 3.0, adjusted with $H_3PO_4$. Identification of trans-resveratrol was based on the retention times of liquid chromatography (FIGS. 7 and 9) and on the similarity of infrared spectra by SCC Coefficient (FIG. 10) and of ultraviolet spectra by Pearson Correlation Coefficient (Table 2). For quantification, an external calibration curve was used, with trans-resveratrol concentrations ranging from 0.10 to 200.00 mg·L$^{-1}$ (FIG. 9). The amount of trans-resveratrol in *Rumex acetosa* roots was 1.2±0.1 mg/g, a high concentration if compared to other known sources of this molecule (Table 1).

TABLE 2

Pearson Correlation Coefficient for the ultraviolet spectra in FIG. 9 (Calculated by SPSS, Version 11.5)

|  |  | Resveratrol | *Rumex acetosa* roots |
|---|---|---|---|
| Resveratrol | Pearson Correlation | 1.0 | 0.986 (**) |
|  | Sig. (2-tailed) |  | 0.0001 |
|  | N | 161 | 161 |

TABLE 2-continued

Pearson Correlation Coefficient for the ultraviolet spectra in FIG. 9
(Calculated by SPSS, Version 11.5)

|  |  | Resveratrol | Rumex acetosa roots |
|---|---|---|---|
| Rumex acetosa roots | Pearson Correlation | 0.986 (**) | 1.0 |
|  | Sig. (2-tailed) | 0.0001 |  |
|  | N | 161 | 161 |

(**) very similar

Products obtained by this unique extraction method, trans-resveratrol and emodin, are active principles that can constitute pharmaceutical compositions presenting antioxidant, anti-inflammatory, antiviral, cardioprotective, neuroprotective, and/or chemoprotective activities, besides protecting against infections and ischemia, treating type 1 and 2 diabetes, reducing obesity and preventing aging. Both products can also constitute food compositions with similar benefits.

The main advantages of the methods herein described are to provide separation and purification of emodin and trans-resveratrol in a unique method with high level of purity for both products. This happens because, as already mentioned, the present invention relates to using a solid-liquid extraction method, Soxhlet type or similar, of *Polygonum cuspidatum* and/or *Rumex acetosa* extracts with different solvents, resulting in a simple and effective method.

Example 3

Preparing a Phytomedicine from *Rumex acetosa* with High Content of Resveratrol

Preparing a resveratrol-rich phytomedicine is useful and necessary for the treatment of several health conditions, especially when current sources of resveratrol are not easily available and/or when new and alternative sources (as observed in present example) provide technically and economically viable therapeutic options for improvement in users' quality of life. The inventors, searching for new and alternative phytomedicines as a way of providing a resveratrol-rich therapeutic option, developed a new phytomedicine from sorrel whose use was not known for this purpose until now. The phytomedicine of the invention is rich in resveratrol and comprises roots and/or rhizomes of *Rumex acetosa* and/or their fractions. For the present invention purposes, fractions of roots and/or rhizomes of *Rumex acetosa* include products obtained by, at least, partial purification and/or extraction of resveratrol present in roots and/or rhizomes. In order to avoid using sorrel leaves that taste like vinegar because of the oxalic acid, the preparation of the phytomedicine described used the roots and/or rhizomes of the plant. *Rumex acetosa* roots and rhizomes were washed and dried in oven at 40° C. or were freeze-dried. Material was triturated in a knife mill until a powder was obtained. Resulting powder (5 g) was extracted with 100 mL of an ethanol/water (70:30) solution for 60 minutes under stirring or by ultrasound. Then the mixture was centrifuged at 1200 g and filtered. Solvent was removed under reduced pressure at 50° C. The product obtained was a paste. Such paste was freeze-dried to obtain a powder of *Rumex acetosa*, with 10-20% of resveratrol, determined by High Performance Liquid Chromatography. An excipient can be optionally added to the powder; the dry mixture provides a resveratrol-rich product extract. The preferred excipients are polysaccharide products, which include, but are not limited to, starch, gelatin, microcrystalline cellulose, chitosan, cellulose, hydroxypropylcellulose (HPC), carboxymethylcellulose (CMC), hydroxypropylmethylcellulose (HPCM), etc. The excipient can also be a cyclic oligosaccharide, such as α-cyclodextrin, β-cyclodextrin, and γ-cyclodextrin derivatives that can be, but are not limited to, hydroxypropyl, hydroxyethyl, glucosyl, maltosyl, maltotriosyl carboxyamidomethyl, carboxymethyl and diethylamino derivatives. In order to obtain granules, sorrel powder is sifted and magnesium stearate is added to it. The mixture is dried and granulated. The resulting product can have tablet, capsule or powder form.

Those skilled in the art will immediately appreciate the important benefits brought by the present invention, such as separation and purification of anthraquinone emodin and/or polyphenol trans-resveratrol with high level of purity, as well as nutraceutical and/or phytotherapic compositions containing any of said actives. It is to be expressly understood that variations in the way of performing the inventive concept here described is to be deemed within the spirit of the invention and the attached claims.

What is claimed is:

1. A process for obtaining trans-resveratrol and/or emodin comprising the selective solid-liquid solvent extraction of Polygonum Cuspidatum and/or *Rumex acetosa* materials, said process comprising the following steps:
    a) extraction with aromatic solvent for obtaining emodin;
    b) extraction with open-chain hydrocarbon and/or ether, both with six atoms of carbon, for eliminating impurities; and
    c) extraction with polar solvent for obtaining trans-resveratrol.

2. The process according to claim 1, wherein said aromatic solvent is toluene.

3. The process according to claim 1, wherein said open-chain hydrocarbon is hexane and said ether is petroleum ether.

4. The process according to claim 1, wherein said polar solvent is diethyl ether.

5. The process according to claim 1, wherein step a) is performed for 2 to 40 hours.

6. The process according to claim 1, wherein said emodin is obtained in the form of crystals, with a yield of 4-6% and purity of 91-96%.

7. The process according to claim 1, wherein step b) is performed for 1 to 2 hours.

8. The process according to claim 1, wherein step c) is performed for 2 to 24 hours.

9. The process according to claim 1, wherein said trans-resveratrol is obtained with a yield of 5-7% and purity of 92-98%.

10. A nutraceutical composition comprising, as active and/or functional component, trans-resveratrol and/or emodin obtained by selective extraction of solid-liquid solvent in material of *Polygonum Cuspidatum* and/or *Rumex acetosa*, said selective solid-liquid solvent extraction comprising the following steps:
    a) extraction with aromatic solvent for obtaining emodin;
    b) extraction with open-chain hydrocarbon and/or ether, both with six atoms of carbon, for eliminating impurities; and
    c) extraction with polar solvent for obtaining trans-resveratrol.

11. The composition according to claim 10, wherein said active and/or functional component(s) is(are) present with purity from 91 to 98%.

12. A phytotherapic composition comprising trans-resveratrol content obtained from roots and/or rhizomes of

*Rumex acetosa* and/or fractions thereof, wherein the trans-resveratrol is obtained by a process comprising the selective solid-liquid solvent extraction of *Polygonum Cuspidatum* and/or *Rumex acetosa* materials, said process comprising the following steps:
 a) extraction with aromatic solvent for obtaining emodin;
 b) extraction with open-chain hydrocarbon and/or ether, both with six atoms of carbon, for eliminating impurities; and
 c) extraction with polar solvent for obtaining trans-resveratrol.

13. A phytomedicine comprising trans-resveratrol obtained from roots and/or rhizomes of *Rumex acetosa* and/or fractions thereof, wherein the trans-resveratrol is obtained by a process comprising the selective solid-liquid solvent extraction of *Polygonum Cuspidatum* and/or *Rumex acetosa* materials, said process comprising the following steps:
 a) extraction with aromatic solvent for obtaining emodin;
 b) extraction with open-chain hydrocarbon and/or ether, both with six atoms of carbon, for eliminating impurities; and
 c) extraction with polar solvent for obtaining trans-resveratrol.

* * * * *